United States Patent
Lim et al.

(10) Patent No.: US 12,220,168 B2
(45) Date of Patent: Feb. 11, 2025

(54) CHART PROJECTOR FOR TESTING VISUAL ACUITY

(71) Applicant: HUVITZ CO., LTD., Anyang-si (KR)

(72) Inventors: Jong Min Lim, Anyang-si (KR); Min Soo Cho, Anyang-si (KR)

(73) Assignee: HUVITZ CO., LTD., Anyang-si (KR)

( * ) Notice: Subject to any disclaimer, the term of this patent is extended or adjusted under 35 U.S.C. 154(b) by 692 days.

(21) Appl. No.: 17/518,913

(22) Filed: Nov. 4, 2021

(65) Prior Publication Data
US 2022/0160226 A1    May 26, 2022

(30) Foreign Application Priority Data

Nov. 25, 2020 (KR) .................. 10-2020-0159752

(51) Int. Cl.
*A61B 3/032* (2006.01)
*A61B 3/00* (2006.01)
*A61B 3/08* (2006.01)

(52) U.S. Cl.
CPC ............ *A61B 3/032* (2013.01); *A61B 3/0041* (2013.01); *A61B 3/08* (2013.01)

(58) Field of Classification Search
CPC .......... A61B 3/08; A61B 3/0041; A61B 3/032
USPC ................................................. 351/201, 246
See application file for complete search history.

(56) References Cited

U.S. PATENT DOCUMENTS

| | | | | |
|---|---|---|---|---|
| 6,361,167 B1 * | 3/2002 | Su | ............ | A61B 3/107 351/206 |
| 2009/0244486 A1 * | 10/2009 | Oda | ............ | A61B 3/032 351/240 |
| 2011/0075099 A1 | 3/2011 | Kanazawa | | |

OTHER PUBLICATIONS

U.S. Appl. No. 17/392,362, filed Aug. 3, 2021, Min Soo Cho.

* cited by examiner

*Primary Examiner* — Robert E. Tallman
(74) *Attorney, Agent, or Firm* — United One Law Group LLC; Kongsik Kim; Jhongwoo Peck

(57) ABSTRACT

A chart projector for testing visual acuity capable of detecting a brightness of a visual acuity chart which is projected to an examined eye includes at least one image display device which produces visual acuity chart image; a beam splitter; and a photo sensor which detects a brightness of the chart image reflected from the beam splitter to determine a brightness of visual acuity chart image which passes the beam splitter and projected to the examined eye or which detects a brightness of the chart image which passes the beam splitter to determine a brightness of visual acuity chart image reflected from the beam splitter and projected to the examined eye.

7 Claims, 5 Drawing Sheets

CHART PROJECTOR FOR TESTING VISUAL ACUITY

CROSS-REFERENCE TO RELATED APPLICATION

This application claims priority to Korean Application No. 10-2020-0159752 filed on Nov. 25, 2020, which is incorporated herein by reference in its entirety.

TECHNICAL FIELD

The present invention relates to a chart projector for testing visual acuity, and more particularly, to a chart projector for testing visual acuity capable of detecting a brightness of a visual acuity chart which is projected to an examined eye.

RELATED ART

Binocular vision is a term that contrasts monocular vision. Binocular vision refers to a method of recognizing an object perceived respectively by both eyes as a single object by the cooperative action of both eyes when gazing at the same location of the object with both eyes. Since the positions of the left and right eyes differ by about 6 cm, the images reflected in the left and right eyes are slightly different even when looking at the same object, which is called binocular parallax (disparity). In spite of this parallax, what we see in general is a single fused image rather than images such as those superimposed, which is called binocular fusion. In other words, if objects of similar shapes are presented to the right and left eyes, respectively, the brain recognizes the existence of one object by fusing the images perceived by both eyes. On the other hand, if objects of completely different shapes are presented to both eyes, the images perceived by both eyes will be recognized separately instead of being fused into one. This is called binocular rivalry.

In order to examine such a binocular vision function, chart projectors for testing visual acuity in which visual acuity charts are intended to be projected to the right eye and the left eye of an examinee, respectively, are known. FIG. 1 is a diagram for illustrating the operating principle of a typical polarized visual acuity chart projector for a binocular vison examination. As shown in FIG. 1, the conventional polarized chart projector comprises an image display device 10 such as an LCD that displays a visual acuity chart of a predetermined shape, and a polarizing film 20 of a sheet shape attached to the front surface of the image display device 10. Polarization regions 20a and 20b of a line shape extending in one direction (horizontal direction in FIG. 1) in correspondence with the pixel size of the image display device 10 are alternately arranged in the polarizing film 20. The polarization regions 20a and 20b comprise a first polarization region 20a and a second polarization region 20b to generate a pair of chart images having polarization axes orthogonal to each other when transmitting the light of a chart image emitted from the image display device 10. The first polarization region 20a is an optical region for the right eye, and the direction of its optical principal-axis is arranged so as to be converted into polarized light having a polarization axis direction (135-degree direction) that coincides with the polarization axis direction of a polarization filter 22a for the right eye. On the other hand, the second polarization region 20b is an optical region for the left eye, and the direction of its optical principal-axis is arranged so as to be converted into polarized light having a polarization axis direction (45-degree direction) that coincides with the polarization axis direction of a polarization filter 22b for the left eye.

In such a polarized visual acuity chart projector, when the image display device 10 is operated so that predetermined chart shapes are displayed on the first polarization region 20a and the second polarization region 20b, and the polarization filter 22a for the right eye and the polarization filter 22b for the left eye are mounted to the right eye and the left eye of the examinee, only the chart images of the first polarization region 20a and the second polarization region 20b are shown to the right and left eyes of the examinee, respectively, and thus, a binocular vision examination can be performed by examining how the examinee recognizes them.

A novel chart projector, which is implementing such polarized charts in a different way, is explained in Korean Patent application No. 10-2020-0104771 (filing date: 2020 Aug. 20) by the present inventors. The polarized chart projector described in the application produces a polarized chart by combining two charts which are separately projected (radiated) from two separate image display devices with a beam splitter (for example, a half mirror). However, since the chart projector produces two charts with two separate image display devices, the brightness of the two charts projected from the two separate image display devices can be different. Also, the brightness of the charts might be decreased when penetrating through the beam splitter or reflecting on the beam splitter and thereby the charts might not have enough brightness for testing visual acuity. Also, as the image display devices would be old and degraded after long-time use, the charts might not have enough brightness for testing visual acuity.

Prior Art Literature

Korean Patent Publication No. 10-2011-0035876 (Apr. 6, 2011)

SUMMARY

Therefore, it is an object of the present invention to provide a chart projector for testing visual acuity capable of detecting a brightness of a visual acuity chart which passes a beam splitter such as a half mirror.

It is another object of the present invention to provide a chart projector for testing visual acuity capable of controlling the brightness of the two charts projected from the two separate image display devices to be the same.

In order to achieve the objects above, the present invention provides a chart projector for testing visual acuity comprising: at least one image display device (30a, 30b) which produces visual acuity chart image (40a, 40b); a beam splitter (50), when the chart image (40a) is produced in a looking direction of an examined eye (5), which transmits a part of the chart image (40a) to the examined eye (5), and reflects the other part of the chart image (40a) to block the other part to be projected to the examined eye (5), and when the chart image (40b) is produced outside of the looking direction of the examined eye (5), which reflects a part of the chart image (40b) so as to be projected to the examined eye (5), and transmits the other part of the chart image (40b) to block the other part to be projected to the examined eye (5); and a photo sensor (60) which detects a brightness of the chart image (40a) reflected from the beam splitter (50) to determine a brightness of visual acuity chart image (40a) which passes the beam splitter (50) and projected to the examined eye (5) or which detects a brightness of the chart image (40b) which passes the beam splitter (50) to determine a brightness of visual acuity chart image (40b) reflected from the beam splitter (50) and projected to the examined eye (5).

The present invention also provides a chart projector for testing visual acuity comprising: a first image display device (30a) which projects a first visual acuity chart image (40a) polarized in a first direction; a second image display device (30b) which projects a second visual acuity chart image (40b) polarized in a second direction; a beam splitter (50) which partially transmits the first visual acuity chart image (40a) emitted from the first image display device (30a) as it is to thereby project the first visual acuity chart image (40a) polarized in the first direction to an examined eye (5), and partially reflects the second visual acuity chart image (40b) polarized in the second direction emitted from the second image display device (30b) to thereby project a second visual acuity chart image (40b) polarized in a third direction different from the first direction to the examined eye (5); and a photo sensor (60) which detects a brightness of the first chart image (40a) which is produced by the first image display devices (30a) and reflected from the beam splitter (50), and thereby determines the brightness of the first chart image (40a) which is projected to the examined eye (5), and which detects a brightness of the second chart image (40b) which is produced by the second image display devices (30b) and passes through the beam splitter (50), and thereby to determine the brightness of the second chart image (40a) which is projected to the examined eye (5).

The chart projector for testing visual acuity in accordance with the present invention can detect a brightness of a visual acuity chart which passes a beam splitter such as a half mirror. Also, the chart projector for testing visual acuity in accordance with the present invention can control the brightness of the two charts projected from the two separate image display devices to be the same.

DETAILED DESCRIPTION

Figure 1:
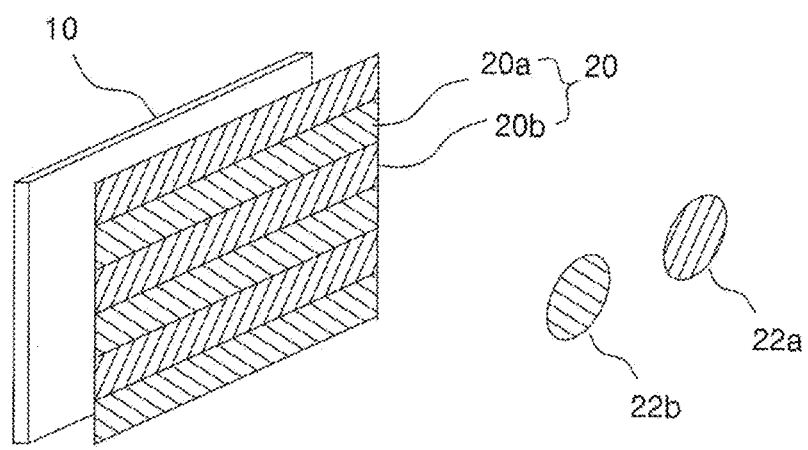
FIG. 1 is a diagram for illustrating the operating principle of a typical polarized visual acuity chart projector for a binocular vison examination.

Hereinafter, the present invention will be described in detail with reference to the accompanying drawings. In the drawings attached, the same reference numerals are assigned to elements that perform the same or similar functions as in the prior art.

Figure 2:
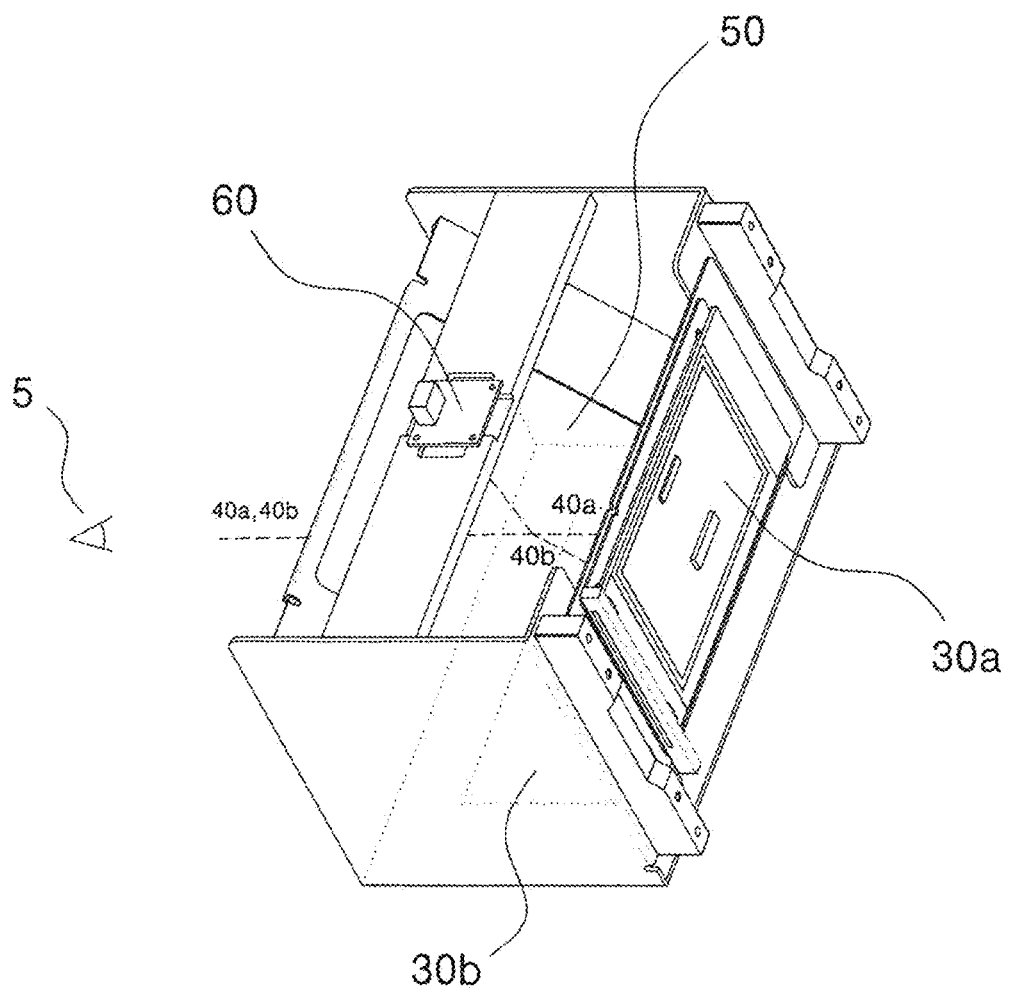
FIGS. 2 and 3 are a perspective view and a cross-sectional view (in light projecting direction) respectively showing the structure of a chart projector for testing visual acuity in accordance with one embodiment of the present invention.
Figure 3:
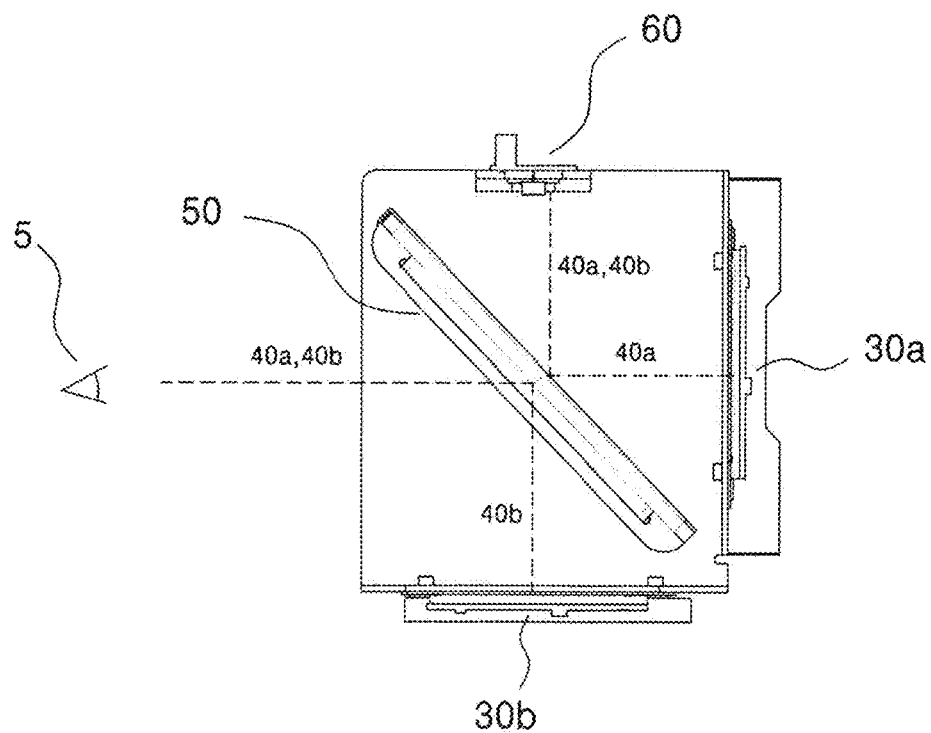

FIGS. 2 and 3 are a perspective view and a cross-sectional view (in a light projecting direction) respectively showing the structure of a chart projector for testing visual acuity in accordance with one embodiment of the present invention. As shown in FIGS. 2 and 3, the chart projector for testing visual acuity in accordance with the present invention includes at least one image display device 30a, 30b, a beam splitter 50 and a photo sensor 60.

The image display device 30a, 30b produces visual acuity chart image 40a, 40b, namely, chart image 40a, 40b for testing visual acuity of an examined eye 5. The image display device 30a, 30b can be any image display device which produces chart image 40a, 40b, and for example, may be a liquid crystal display device (LCD) or an organic light emitting device (OLED). The produced chart image 40a, 40b penetrates the beam splitter 50 or reflects from the beam splitter 50 according to the projection directions of the chart images 40a, 40b, and is projected to the examined eye 5. Specifically, when the chart image 40a is produced in the looking direction of the examined eye 5, the beam splitter 50 transmits a part of the chart image 40a to the examined eye 5, and reflects the other part of the chart image 40a to block the other part to be projected to the examined eye 5. When the chart image 40b is produced outside of the looking direction of the examined eye 5 (for example, in an orthogonal direction of the looking direction), the beam splitter 50 reflects a part of the chart image 40b so as to be projected to the examined eye 5, and transmits the other part of the chart image 40b to block the other part to be projected to the examined eye 5. For example, the first image display devices 30a, which is positioned in the looking direction of the examined eye 5, produces visual acuity chart image 40a which penetrates the beam splitter 50 and is projected to the examined eye 5. Meanwhile, the second image display devices 30b, which is positioned outside of the looking direction of the examined eye 5, produces visual acuity chart image 40b which reflects from the beam splitter 50 and is projected to the examined eye 5.

The beam splitter 50 is a typical device that reflects some of an incident light and transmits some of the incident light, may be, for example, a pair of prisms joined in a hexahedral shape, a half mirror, a dichroic mirrored prism, etc., and preferably a half mirror. The brightness of chart image reflected from the beam splitter 50 and the brightness of chart image passes (i.e., penetrates) the beam splitter 50 are varied according to the light transmission/reflection ratio of the beam splitter 50. However, it is preferred that, when the brightness of chart image projected to the beam splitter 50 is 100, the brightness of chart image reflected from the beam splitter Sand the brightness of chart image passes the beam splitter 50 are same, namely, are respectively 50 (i.e., 50% of the projected light is transmitted and the other 50% is reflected). As explained, since the chart image 40a, 40b produced by the image display device 30a, 30b is divided either by passing the beam splitter 50 or by reflecting from the beam splitter 50, the brightness of the chart image 40a, 40b projected to the examined eye 5 decreases, and could be less than the necessary brightness for a visual acuity chart projector, for example, could be less than 80 to 320 cd/m2. In such case, the brightness of the chart image 40a, 40b needs to be increased by the image display devices 30a, 30b. Therefore, in the chart projector for testing visual acuity according to the present invention, the brightness of the visual acuity chart image 40a, 40b produced by the image display devices 30a, 30b is controlled according to the brightness of the visual acuity chart images 40a, 40b detected by the photo sensor 60.

The photo sensor 60 detects (measures) the brightness of the chart image 40a reflected from the beam splitter 50 (for example, see dotted line 40a in FIG. 4) to determine the brightness of visual acuity chart image 40a which passes the beam splitter 50 (for example, see solid line 40a in FIG. 4) and projected (radiated) to the examined eye 5. Also, the photo sensor 60 detects (measures) the brightness of the chart image 40b which passes the beam splitter 50 (for example, see dotted line 40b in FIG. 4) to determine the brightness of visual acuity chart image 40b reflected from the beam splitter 50 (for example, see solid line 40b in FIG. 4) and projected (radiated) to the examined eye 5. As described above, the brightness of chart image 40a, 40b produced by the image display devices 30a, 30b is divided with a predetermined ratio at the beam splitter 50. Thus, when the brightness of chart image 40a, 40b which is reflected from or passes the beam splitter 50 is measured, the brightness of chart image 40a, 40b which passes or is reflected from the beam splitter 50 can be calculated. Specifically, the visual acuity chart image 40a is produced by the first image display devices 30a positioned at the looking direction of the examined eye 5, and the produced chart image 40a is divided at the beam splitter 50. In this case, when the brightness of chart image 40a reflected from the beam splitter 50 is detected, the brightness of chart image 40a passes through the beam splitter 50 and projected to the examined eye 5 can be determined. Similarly, the visual acuity chart image 40b is produced by the second image display devices 30b positioned outside of the looking direction of the examined eye 5, and the produced chart image 40b is divided at the beam splitter 50. In this case, when the brightness of chart image 40b passes through the beam splitter 50 is detected, the brightness of chart image 40b reflected from the beam splitter 50 and projected to the examined eye 5 can be determined. According to the present invention, the brightness of chart image 40a, 40b which is not projected to the examined eye 5 is detected to indirectly detect (i.e., determine) the brightness of chart image 40a, 40b which is projected to the examined eye 5. Thus, the photo sensor 60 can be located outside of the projection path of the chart image 40a, 40b projected to the examined eye 5. After determining the brightness of chart image 40a, 40b projected to the examined eye 5, when the brightness of chart image 40a, 40b is out of a predetermined range, the brightness of the image display device 30a, 30b, namely, the brightness of chart image 40a, 40b produced by the image display device 30a, 30b is manually or automatically controlled in order to adjust the brightness of chart image 40a, 40b which is projected to the examined eye 5 to be within the predetermined range.

Figure 4:
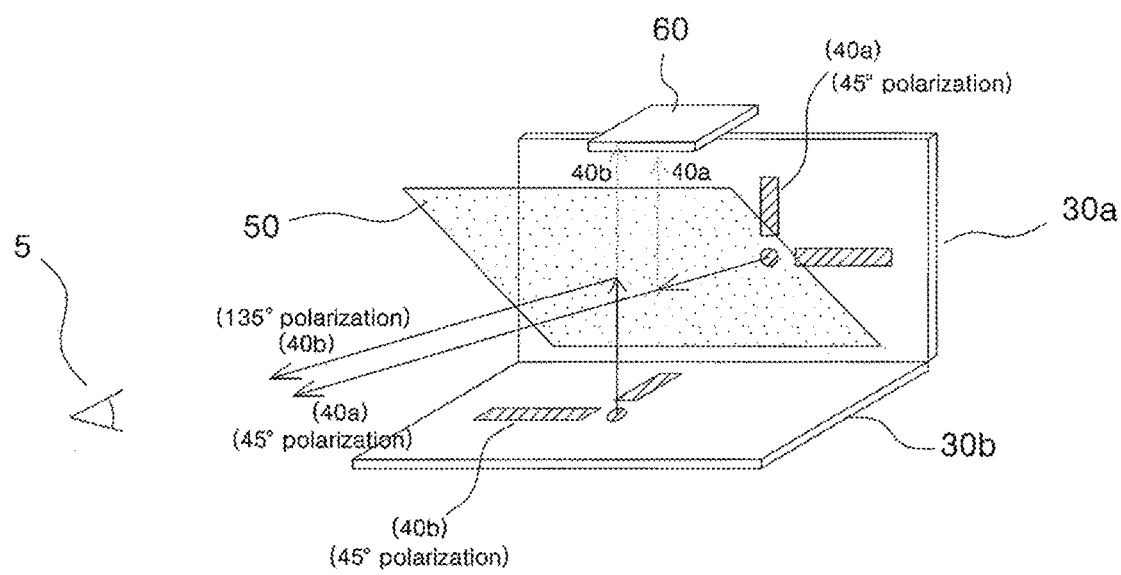
FIG. 4 is a diagram showing the structure of a chart projector for testing visual acuity in accordance with another embodiment of the present invention.

FIG. 4 is a diagram showing the structure of a chart projector for testing visual acuity in accordance with another embodiment of the present invention, in which the chart projector for testing visual acuity of the present invention is used for a binocular vision examination. As shown in FIG. 4, the first image display device 30a projects a first visual acuity chart image 40a polarized in a first direction, and the second image display device 30b projects a second visual acuity chart image 40b polarized in a second direction. The beam splitter 50 partially transmits the first visual acuity chart image 40a emitted from the first image display device 30a as it is (i.e., without changing the polarization direction) to thereby project the first visual acuity chart image 40a polarized in the first direction to the examined eye 5, and partially reflects the second visual acuity chart image 40b polarized in the second direction emitted from the second image display device 30b to thereby project a second visual acuity chart image 40b polarized in a third direction different from the first direction to the examined eye 5.

For a binocular vision examination, since the first visual acuity chart image 40a that is emitted from the first image display device 30a and is projected in the direction of the examined eye 5 should be recognized by only one of both eyes of the examinee and the second visual acuity chart image 40b that is emitted from the second image display device 30b and is projected in the direction of the examined eye 5 should be recognized by only the other of both eyes of the examinee, the first polarization direction of the first visual acuity chart image 40a and the third polarization direction of the second visual acuity chart image 40b should be different from each other. For example, as shown in FIG. 4, if the first polarization direction of the first visual acuity chart image 40a emitted from the first image display device 30a is 45 degrees, then the polarization direction of the first visual acuity chart image 40a that has passed through the beam splitter 50 is also 45 degrees, and thus, the examinee recognizes the first visual acuity chart image 40a polarized at 45 degrees. On the other hand, if the second polarization direction of the second visual acuity chart image 40b emitted from the second image display device 30b is 45 degrees, then the polarization direction (third direction) of the second visual acuity chart image 40b that has been specular-reflected by the beam splitter 50 is 135 degrees, and thus, the examinee recognizes the second visual acuity chart image 40b polarized at 135 degrees. If polarized light is reflected by a mirror, its polarization angle is changed. For example, if light polarized at 45 degrees is reflected by a mirror at a reflection angle of 90 degrees, then light polarized at 135 degrees is reflected. The present invention generates the chart images 40a and 40b with different polarization directions using these characteristics.

At this time, the photo sensor 60 detects the brightness of the first chart image 40a which is produced by the first image display devices 30a and reflected from the beam splitter 50, and thereby determines the brightness of the first chart image 40a which is projected to the examined eye 5. Also, the photo sensor 60 detects the brightness of the second chart image 40b which is produced by the second image display devices 30b and passes through the beam splitter 50, and determine the brightness of the second chart image 40a which is projected to the examined eye 5. For accurate measurement of the brightness, when detecting the brightness of the first chart image 40a which is produced by the first image display devices 30a, the second image display devices 30b is turned off. Also, when detecting the brightness of the second chart image 40b which is produced by the second image display devices 30b, the first image display devices 30a is turned off. As shown in FIG. 4, when producing the chart images 40a, 40b having different polarization directions with the first and the second image display devices 30a, 30b, the brightness of the first and the second chart images 40a, 40b might be different from each other due to the instrumental differences of the first image display devices 30a and the second image display devices 30b. Also, as the intensity of the first and the second chart images 40a, 40b decreases while passing through the beam splitter 50 such as a half mirror or while reflecting from the beam splitter 50, the brightness of the first and the second chart images 40a, 40b projected to the examined eye 5 might not have the necessary brightness for the chart projector for testing visual acuity, for example, a uniform brightness of 80 to 320 cd/m$^2$. In case that the brightness of the first and the second chart images 40a, 40b are different, for example, if the brightness of the first chart image 40a is 80 cd/m$^2$, and the brightness of the second chart image 40b is 320 cd/m$^2$, the visual acuity test using the polarization images might be inaccurate. Thus, according to the present invention, the brightness of the first and the second chart images 40a, 40b are preferably controlled to be more than a predetermined reference value, for example, more than 200 cd/m$^2$ (ISO standard: ISO-8596, Third edition, 2017-11, p 5, 4.6 Luminance). Thus, in this embodiment, according to the brightness of the visual acuity chart images 40a, 40b detected with the photo sensor 60, the brightness of the first and the second chart images 40a, 40b projected to the examined eye 5 can be controlled to be same.

Figure 5A:
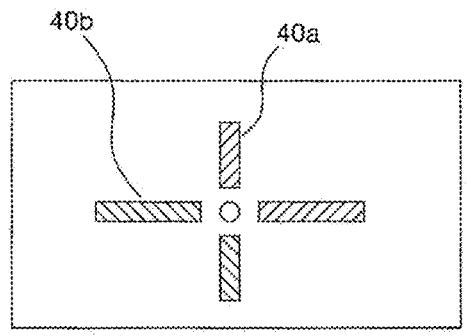
FIGS. 5A-5C are diagrams showing states in which an examinee recognizes polarized charts emitted from the chart projector shown in FIG. 4.
Figure 5B:
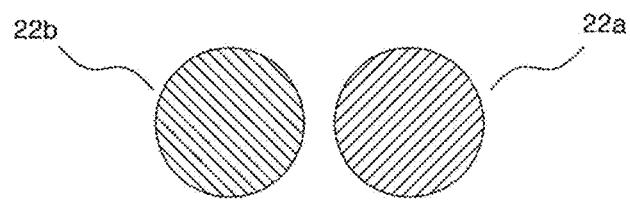
Figure 5C:
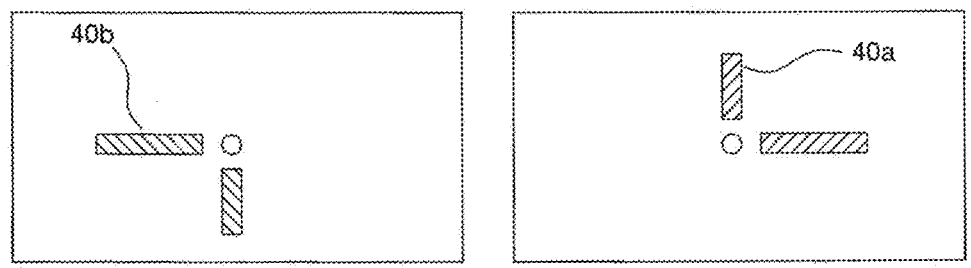

FIGS. 5A-5C are diagrams showing states in which an examinee recognizes polarized charts emitted from the chart projector shown in FIG. 4. As shown in FIG. 5A, a polarized visual acuity chart projector shown in FIG. 4 projects a first visual acuity chart image 40a polarized in a first polarization direction (45 degrees in FIGS. 5A-5C) and a second visual acuity chart image 40b polarized in a third polarization direction (135 degrees in FIGS. 5A-5C). At this time, if a polarization filter 22a for the right eye polarized in the first polarization direction (45 degrees in FIGS. 5A-5C) is mounted to the right eye of an examinee (FIG. 5B), then the first visual acuity chart image 40a polarized in the first polarization direction (45 degrees in FIGS. 5A-5C) is recognized by the right eye of the examinee, but the second visual acuity chart image 40b polarized in the third polarization direction (135 degrees in FIGS. 5A-5C) is blocked and cannot be recognized (FIG. 5C). Likewise, if a polarization filter 22b for the left eye polarized in the third polarization direction (135 degrees in FIGS. 5A-5C) is mounted to the left eye of the examinee (FIG. 5B), then the second visual acuity chart image 40b polarized in the third polarization direction (135 degrees in FIGS. 5A-5C) is recognized by the left eye of the examinee, but the first visual acuity chart image 40a polarized in the first polarization direction (45 degrees in FIGS. 5A-5C) is blocked and cannot be recognized (FIG. 5C). Therefore, by projecting different chart images to the right eye and the left eye of the examinee, the binocular vision examination can be performed for the examinee.

In the polarized visual acuity chart projector in accordance with the present invention, the difference between the first polarization direction of the first visual acuity chart image 40a and the third polarization direction of the second visual acuity chart image 40b is provided so that, when mounting the polarization filter 22a for the right eye and the polarization filter 22b for the left eye having different polarization directions to the right eye and left eye of the examinee, respectively, one of the first visual acuity chart image 40a and the second visual acuity chart image 40b can be recognized only by the right eye and the other can be recognized only by the left eye. If the first polarization direction and the third polarization direction are the same or the difference therebetween is small (for example, 45 degrees or less), even if the polarization filter 22a for the right eye and the polarization filter 22b for the left eye having different polarization directions are mounted, chart images of other than the intended charts can be projected onto each of the eyes to be examined. Preferably, it is desirable when there is a 90-degree difference between the first polarization direction and the third polarization direction and there is also a 90-degree difference between the polarization directions of the polarization filter 22a for the right eye and the polarization filter 22b for the left eye. This is because that, at this time, chart images other than the intended charts can be most completely blocked from being projected.

If the image display device is an image display device that does not have polarization such as OLEDs, a polarization filter polarized with a predetermined angle may be attached to the image display device so as to produce polarized chart images. If the image display device is a liquid crystal display device (LCD) or the like that projects a polarized image by itself by including a polarizing film in its internal structure, it can be used as it is without attaching a additional polarizing film. Thus, the first image display device 30a and the second image display device 30b are preferably a liquid crystal display device that projects a polarized image. For example, since small (5.7 or 5 inch) LCDs used in smartphones, etc. generally have a polarization angle of 45 degrees, it can be used as it is without attaching an additional polarizing film. However, if the degree of polarization of a commercially available LCD module is not enough, a polarizing film of a corresponding angle may also be additionally attached and used.

In a preferred embodiment of the present invention, as shown in FIG. 4, the first image display device 30a and the second image display device 30b are arranged so as to face each other at an angle of 90 degrees, and the beam splitter 50 is arranged between the first image display device 30a and the second image display device 30b at an angle of 45 degrees. In addition, the photo sensor 60 is preferably positioned in the projection direction of chart image 40a which is reflected from the beam splitter 50 and does not being projected to the examined eye 5. Also the photo sensor 60 is preferably positioned in the projection direction of chart image 40b which passes through the beam splitter 50 and does not being projected to the examined eye 5. Preferably, the first image display devices 30a and the second image display devices 30b produce the first chart image 40a having polarization angle of 45 degree and the second chart image 40b having polarization angle of 45 degree. The first chart image 40a having polarization angle of 45 degree passes through the beam splitter 50 and is projected to the examinee as it is. The second chart image 40b having polarization angle of 45 degree is reflected from the beam splitter 50 and then the second chart image 40b having polarization angle of 135 degree is projected to the examinee. The first chart image 40a having polarization angle of 45 degree passes and the second chart image 40b having polarization angle of 135 degree are preferably projected to the examinee in parallel.

Although the present invention has been described above with reference to exemplary embodiments, the present invention is not limited to the embodiments described above. The scope of the claims that follow should be construed to encompass all variations, equivalent constructions and functions of the exemplary embodiments. In the appended claims, the reference numerals are added for easy understanding of the claims. However, the scopes of the claims is not limited by the reference numerals and/or the appended drawings.

What is claimed is:
1. A chart projector for testing visual acuity, comprising:
at least one image display device (30a, 30b) which produces visual acuity chart image (40a, 40b) comprising at least a first chart image (40a) and a second chart image (40b);
a beam splitter (50), when the first chart image (40a) is produced in a looking direction of an examined eye (5), which transmits a part of the first chart image (40a) to the examined eye (5), and reflects the other part of the first chart image (40a) to block the other part to be projected to the examined eye (5), and when the second chart image (40b) is produced outside of the looking direction of the examined eye (5), which reflects a part of the second chart image (40b) so as to be projected to the examined eye (5), and transmits the other part of the second chart image (40*b*) to block the other part to be projected to the examined eye (5); and a photo sensor (60) which detects a brightness of the first chart image (40*a*) reflected from the beam splitter (50) to determine a brightness of the first chart image (40*a*) which passes the beam splitter (50) and projected to the examined eye (5) or which detects a brightness of the second chart image (40*b*) which passes the beam splitter (50) to determine a brightness of the second chart image (40*b*) reflected from the beam splitter (50) and projected to the examined eye (5), wherein, when the photo sensor (60) detects the brightness of the first chart image (40*a*) reflected from the beam splitter (50), the second chart image (40*b*) is turned off, and when the photo sensor (60) detects the brightness of the second chart image (40*b*) which passes the beam splitter (50), the first chart image (40*a*) is turned off.

2. The chart projector for testing visual acuity of claim 1, wherein the photo sensor (60) is positioned in a direction perpendicular to a direction that the first chart image (40*a*) is transmitted through the beam splitter (50) and projected to the examined eye (5) or is positioned in a projection direction of the second chart image (40*b*) which passes through the beam splitter (50).

3. The chart projector for testing visual acuity of claim 1, wherein the beam splitter (50) is a half mirror that reflects some of an incident light and transmits some of the incident light.

4. The chart projector for testing visual acuity of claim 1, wherein a brightness of the visual acuity chart image (40*a*, 40*b*) produced by the image display devices (30*a*, 30*b*) is controlled according to the brightness of the visual acuity chart images (40*a*, 40*b*) detected by the photo sensor (60).

5. A chart projector for testing visual acuity, comprising:
a first image display device (30*a*) which projects a first visual acuity chart image (40*a*) polarized in a first direction;
a second image display device (30*b*) which projects a second visual acuity chart image (40*b*) polarized in a second direction;
a beam splitter (50) which partially transmits the first visual acuity chart image (40*a*) emitted from the first image display device (30*a*) as it is to thereby project the first visual acuity chart image (40*a*) polarized in the first direction to an examined eye (5), and partially reflects the second visual acuity chart image (40*b*) polarized in the second direction emitted from the second image display device (30*b*) to thereby project a second visual acuity chart image (40*b*) polarized in a third direction different from the first direction to the examined eye (5); and a photo sensor (60) which detects a brightness of the first chart image (40*a*) which is produced by the first image display devices (30*a*) and reflected from the beam splitter (50), and thereby determines the brightness of the first chart image (40*a*) which is projected to the examined eye (5), and which detects a brightness of the second chart image (40*b*) which is produced by the second image display devices (30*b*) and passes through the beam splitter (50), and thereby to determine the brightness of the second chart image (40*a*) which is projected to the examined eye (5), wherein, when detecting the brightness of the first chart image (40*a*) which is produced by the first image display devices (30*a*), the second image display devices (30*b*) is turned off, and when detecting the brightness of the second chart image (40*b*) which is produced by the second image display devices (30*b*), the first image display devices (30*a*) is turned off.

6. The chart projector for testing visual acuity of claim 5, wherein the first image display device (30*a*) and the second image display device (30*b*) are a liquid crystal display device that projects a polarized image.

7. The chart projector for testing visual acuity of claim 5, wherein, according to the brightness of the visual acuity chart images (40*a*, 40*b*) detected with the photo sensor (60), the brightness of the first and the second chart images (40*a*, 40*b*) projected to the examined eye (5) is controlled to be same.

\* \* \* \* \*